United States Patent [19]

Rosen

[11] 4,245,907
[45] Jan. 20, 1981

[54] DISPOSABLE BLOOD CHAMBER

[75] Inventor: Julius S. Rosen, Buffalo, N.Y.

[73] Assignee: American Optical Corporation, Southbridge, Mass.

[21] Appl. No.: 43,571

[22] Filed: May 29, 1979

[51] Int. Cl.³ .............................................. G01N 21/03
[52] U.S. Cl. ..................................... 356/244; 350/95; 356/246
[58] Field of Search ................... 356/246, 244, 39, 40; 350/95

[56] References Cited

U.S. PATENT DOCUMENTS

| 2,482,650 | 9/1949 | Brown et al. | 356/42 |
| 4,126,418 | 11/1978 | Reese | 356/246 |

Primary Examiner—Vincent P. McGraw
Attorney, Agent, or Firm—Alan H. Spencer

[57] ABSTRACT

A two piece disposable blood chamber having registration means and a locking clip to prevent disassembly for sterilization is disclosed.

4 Claims, 4 Drawing Figures

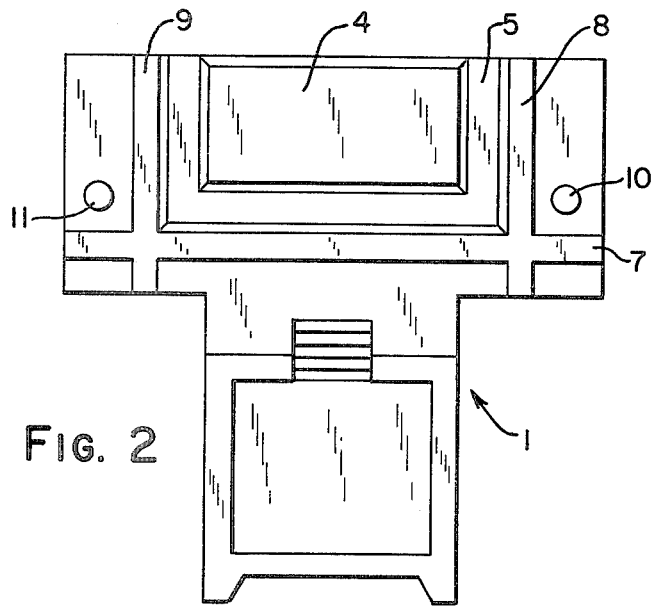
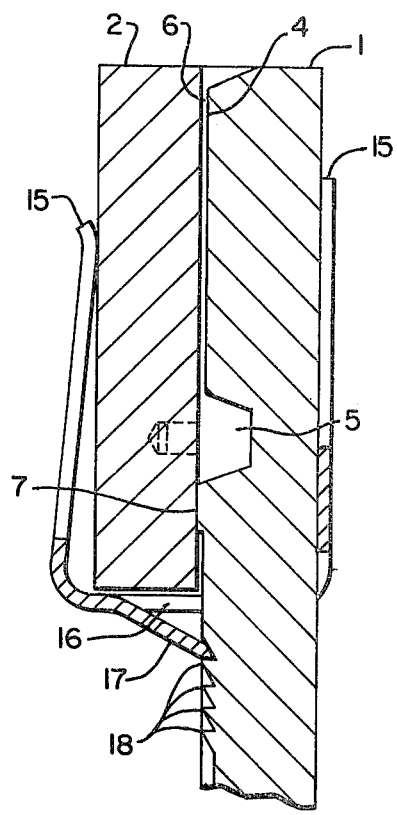
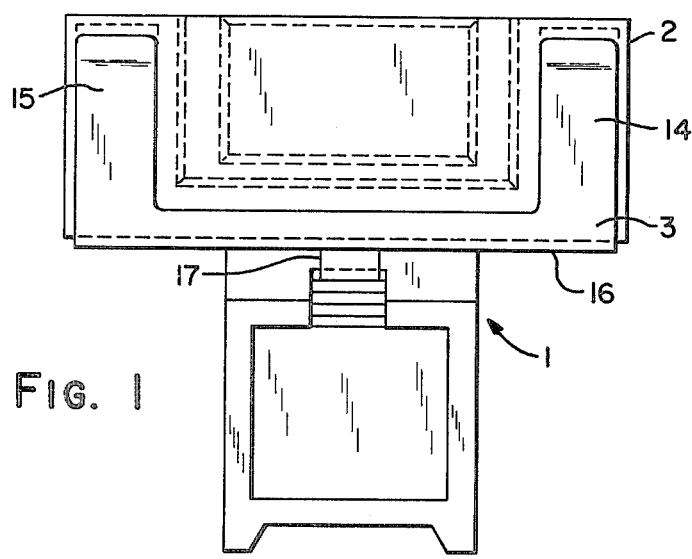
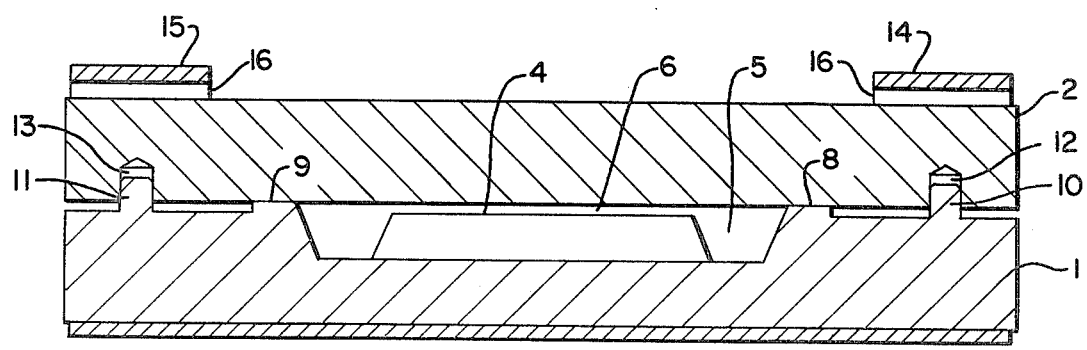

DISPOSABLE BLOOD CHAMBER

BACKGROUND OF THE INVENTION

The present invention relates to disposable blood chambers and more particularly to disposable blood chambers suitable for use in the colormetric determination of hemoglobin and billirubin.

Photometric instruments are used for colorimetry of various liquids, including blood samples. Such instruments of specialized use with blood samples include hemoglobinometers and billirubinometers. An example of a hemoglobinometer in which the present invention may be used is described in U.S. Pat. No. 2,482,650, issued on Sept. 20, 1949 to Morden G. Brown and Harry F. Lundberg. The details of this instrument will not be further described herein except insofar as necessary to an understanding of this invention.

In the Brown and Lundberg patent, the liquid (blood) sample is introduced into the photometer by a sample chamber of three parts, best shown in FIGS. 8 and 9 of the patent. These parts include a lower glass plate defining certain channels, an an upper glass plate which fits on the lower plate to define therewith a capillary chamber of precise thickness. The two plates are held together by a spring clip having a handle by which the plates are inserted into, and removed from, the instrument. The capillary chamber holds the blood sample for photometric analysis. The glass plates are retained and washed between successive use. Their use involves the manipulating of three separate parts in addition to the blood sample itself.

U.S. Pat. No. 3,565,537 discloses a two piece chamber construction where the pieces are joined by ultrasonic welding.

U.S. Pat. No. 3,705,000 discloses a one piece chamber having a well for temporarily holding a blood sample.

Neither the welded two piece construction or unitary one piece chamber has been acceptable because of the requirement for exceptionally close tolerances in the capillary chamber which cannot be consistently achieved on a commercial scale. The three piece construction having glass chamber halves has been well accepted, but its high cost requires that it be reused. Increasing labor costs and the possibility of cross-contamination have increased the demand for a disposable chamber.

It is an object of the present invention to provide a disposable blood chamber.

It is another object of the present invention to provide an imexpensive disposable blood chamber without sacrificing accurate chamber dimensions.

It is still another object of the present invention to provide a blood chamber that cannot be disassembled for sterilization and reuse.

BRIEF DESCRIPTION OF THE PRESENT INVENTION AND DRAWINGS

A two piece blood chamber having registration means to prevent relative sliding motion between the chamber halves, a clip to urge the chamber halves into engagement and a lock to prevent clip removal. Since the clip cannot be removed, the chamber halves cannot be taken apart for sterilization and the chamber must be discarded. In the preferred embodiment, the clip has a pawl that springs into a recess in one chamber half as the clip is slid over the assembled chamber halves.

FIG. 1 is a top view of the disposable blood chamber of the present invention;

FIG. 2 is a top view of the lower chamber half;

FIG. 3 is a front sectional view of the blood chamber; and

FIG. 4 is a side sectional view of the blood chamber.

DETAILED DESCRIPTION OF THE PRESENT INVENTION AND PREFERRED EMBODIMENT

Referring to FIG. 1, lower chamber half 1 and upper chamber half 2 are held together as an assembly by spring clip 3. Upper chamber half 2 is a rectangular planar plate with particularly careful attention to maintain a planar surface on the side toward lower chamber half 1. Details of lower chamber half 1 are shown in FIG. 2 in conjunction with FIGS. 3 and 4. Planar face 4 is surrounded on three sides by moat 5. Capillary chamber 6 results from support of upper chamber half 2 on ribs 7, 8 and 9 extending above planar face 4. Ribs 7, 8 and 9 are produced with particular care to maintain parallelism with planar face 4. Pins 10 and 11 extend from lower chamber half 1 into corresponding recesses 12 and 13 in upper chamber half 2. Pins 10 and 11 and recesses 12 and 13 cooperate to prevent relative sliding motion between chamber halves 1 and 2.

Spring clip 13 has two pairs of fingers 14 and 15 extending from back 16 for maintaining lower chamber half 1 and upper chamber half 2 in assembled contact. Pawl 17 extends downwardly from back 16 and engages ratchet teeth 18 to prevent subsequent removal of spring clip 3 and disassembly of chamber halves 1 and 2.

What is claimed is:

1. A disposable blood chamber which comprises complementary molded chamber halves for forming a chamber therebetween when assembled in engagement with each other, registration means for restricting sliding motion between assembled chamber halves, clip means for retaining said chamber halves in assembled engagement and lock means for preventing removal of said slip means.

2. A disposable blood chamber according to claim 1 wherein a handle member extends from one of said chamber halves and said lock means engages said member to prevent removal of said clip means.

3. A disposable blood chamber according to claim 2 wherein said lock means protrudes from said clip means and penetrates a recess in said member.

4. A disposable blood chamber according to claim 2 wherein said lock means includes a pawl extending from said clip means and ratchet teeth in said member.

* * * * *